United States Patent
Moein

(10) Patent No.: US 6,572,644 B1
(45) Date of Patent: Jun. 3, 2003

(54) STENT MOUNTING DEVICE AND A METHOD OF USING THE SAME TO COAT A STENT

(75) Inventor: Mohammed E. Moein, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 4 days.

(21) Appl. No.: 09/894,242

(22) Filed: Jun. 27, 2001

(51) Int. Cl.[7] .................................................. A61F 2/06
(52) U.S. Cl. ..................................... 623/1.11; 623/1.15
(58) Field of Search .................................. 623/1.1, 1.11, 623/1.15, 1.23, 1.34, 1.42, 1.46, 1.47; 606/108, 198; 427/2.25, 2.24, 2.28, 2.3, 358

(56) References Cited

U.S. PATENT DOCUMENTS

| | | | |
|---|---|---|---|
| 4,733,665 A | | 3/1988 | Palmaz |
| 4,800,882 A | | 1/1989 | Gianturco |
| 4,886,062 A | | 12/1989 | Wiktor |
| 5,788,626 A | * | 8/1998 | Thompson .................. 623/1.11 |
| 5,895,407 A | * | 4/1999 | Jayaraman ................... 606/198 |
| 5,897,911 A | | 4/1999 | Loeffler ...................... 427/2.25 |
| 5,922,393 A | * | 7/1999 | Jayaraman .................... 427/2.3 |
| 6,010,573 A | * | 1/2000 | Bowlin ....................... 427/2.25 |
| 6,120,847 A | * | 9/2000 | Yang et al. ................... 427/2.1 |
| 6,153,252 A | * | 11/2000 | Hossainy et al. ........... 427/2.25 |
| 6,258,121 B1 | * | 7/2001 | Yang et al. ................. 623/1.11 |
| 6,322,847 B1 | * | 11/2001 | Zhong et al. ............... 427/2.28 |
| 6,364,903 B2 | * | 4/2002 | Tseng et al. ................ 623/1.15 |
| 6,387,118 B1 | * | 5/2002 | Hanson ...................... 623/1.11 |

OTHER PUBLICATIONS

Plaridel K. Villareal, A Stent Mounting Device And A Method Of Using The Same To Coat A Stent, May 31, 2001, Ser. No. 09/873,020.

Inventor: Plaridel K. Villareal; Application Ser. No.: 09/873,020; Filed May 31, 2001; Title: A Stent Mounting Device And A Method Of Using The Same To Coat A Stent.

* cited by examiner

*Primary Examiner*—Gloria M. Hale
(74) *Attorney, Agent, or Firm*—Squire, Sanders & Dempsey, L.L.P.

(57) ABSTRACT

A stent mounting device and a method of coating a stent using the device are provided.

24 Claims, 2 Drawing Sheets

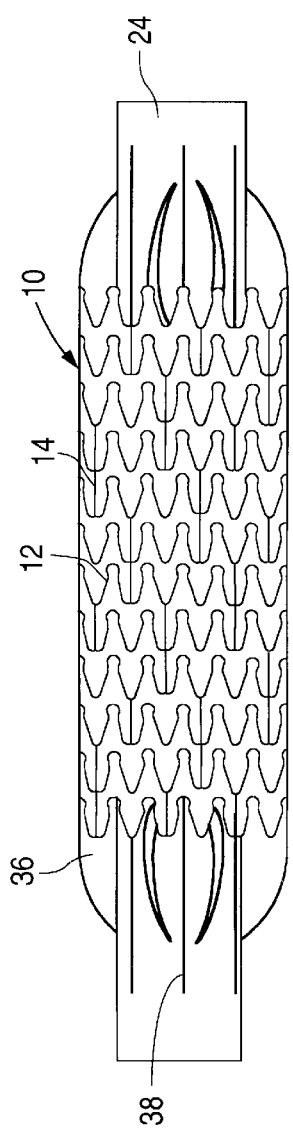
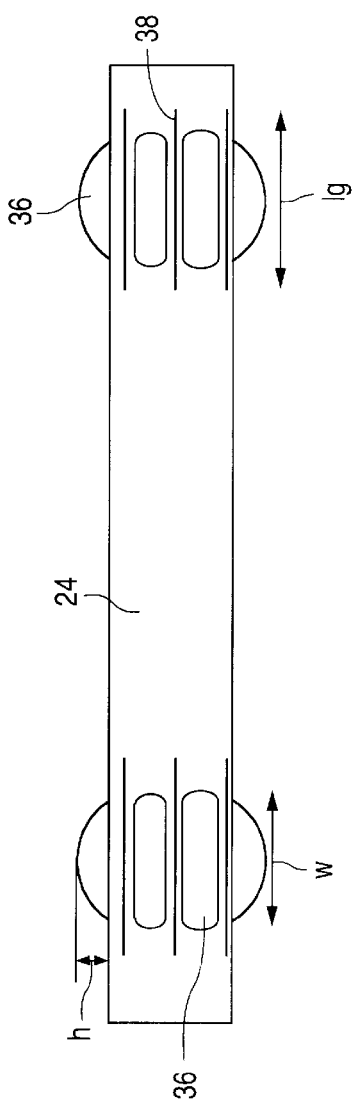
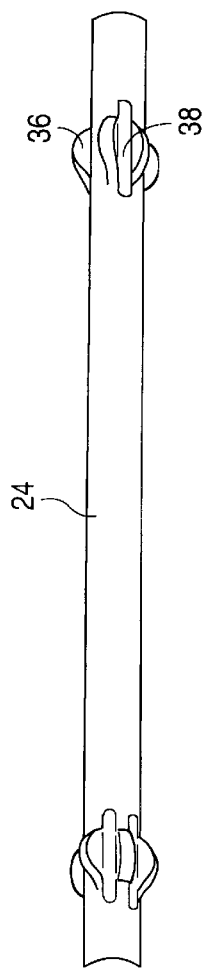
FIGURE 3
FIGURE 4A
FIGURE 4B understand # STENT MOUNTING DEVICE AND A METHOD OF USING THE SAME TO COAT A STENT

BACKGROUND OF THE INVENTION

1. Field of the Invention

This invention relates to a stent mounting device and a method of coating a stent using the device.

2. Description of the Background

Blood vessel occlusions are commonly treated by mechanically enhancing blood flow in the affected vessels, such as by employing a stent. Stents act as scaffoldings, functioning to physically hold open and, if desired, to expand the wall of the passageway. Typically stents are capable of being compressed, so that they can be inserted through small lumens via catheters, and then expanded to a larger diameter once they are at the desired location. Examples in the patent literature disclosing stents include U.S. Pat. No. 4,733,665 issued to Palmaz, U.S. Pat. No. 4,800,882 issued to Gianturco, and U.S. Pat. No. 4,886,062 issued to Wiktor.

FIG. 1 illustrates a conventional stent 10 formed from a plurality of struts 12. The plurality of struts 12 are radially expandable and interconnected by connecting elements 14 that are disposed between adjacent struts 12, leaving lateral openings or gaps 16 between adjacent struts 12. Struts 12 and connecting elements 14 define a tubular stent body having an outer, tissue-contacting surface and an inner surface. Struts 12 that are located at the respective ends of the tubular stent body are referred to herein as end rings 18.

Stents are used not only for mechanical intervention but also as vehicles for providing biological therapy. Biological therapy can be achieved by medicating the stents. Medicated stents provide for the local administration of a therapeutic substance at the diseased site. Local delivery of a therapeutic substance is a preferred method of treatment because the substance is concentrated at a specific site and thus smaller total levels of medication can be administered in comparison to systemic dosages that often produce adverse or even toxic side effects for the patient.

One method of medicating a stent involves the use of a polymeric carrier coated onto the surface of the stent. A composition including a solvent, a polymer dissolved in the solvent, and a therapeutic substance dispersed in the blend is applied to the stent by immersing the stent in the composition or by spraying the composition onto the stent. The solvent is allowed to evaporate, leaving on the stent strut surfaces a coating of the polymer and the therapeutic substance impregnated in the polymer.

A shortcoming of the above-described method of medicating a stent is the potential for coating defects. While some coating defects can be minimized by adjusting the coating parameters, other defects occur due to the nature of the interface between the stent and the apparatus on which the stent is supported during the coating process. A high degree of surface contact between the stent and the supporting apparatus can provide regions in which the liquid composition can flow, wick, and collect as the composition is applied. As the solvent evaporates, the excess composition hardens to form excess coating on or between the stent struts. Upon the removal of the coated stent from the supporting apparatus, the excess coating may stick to the apparatus, thereby removing some of the coating from the stent and leaving bare areas. Alternatively, the excess coating may stick to the stent, thereby leaving excess coating as clumps or pools on the struts or webbing between the struts.

Thus, it is desirable to minimize the interface between the stent and the apparatus supporting the stent during the coating process to minimize coating defects. Accordingly, the present invention provides for a device for supporting a stent during the coating application process. The invention also provides for a method of coating the stent supported by the device.

SUMMARY OF THE INVENTION

The present invention provides a device for supporting a stent during the application of a coating to the stent. The method includes a body configured to penetrate at least partially into the stent and members protruding out from the body for preventing any contact between the inner surface of the stent and the outer surface of the body. The members can be arranged about the circumference of the body and can be circular in shape. In one embodiment, the device additionally includes slots in the outer surface of the body for receiving some of the coating material that comes into contact with the body.

Also provided is a mandrel for supporting a stent. The mandrel includes a body for being at least partially inserted in a hollow body of a stent. The mandrel also includes at least two members projecting out of the body and capable of being in contact with the inner surface of the stent. In one embodiment, the mandrel additionally includes grooves positioned in the body for receiving and containing excess coating substance applied to the stent.

The present invention also provides a method of coating a stent. The method includes positioning a stent over a mandrel having members projecting out of the mandrel, wherein at least one of the members is in contact with the inner surface of the stent. The method also includes applying a coating material to the stent.

BRIEF DESCRIPTION OF THE FIGURES

FIG. 3 illustrates the interface of the spines with the stent.

FIG. 4A illustrates the mandrel of the mounting assembly, illustrating the spines and the optional grooves thereon in accordance with embodiments of the present invention.

FIG. 4B is a perspective view of the mandrel in FIG. 4A.

DETAILED DESCRIPTION

Embodiments of the Stent Mounting Assembly

Figure 2:
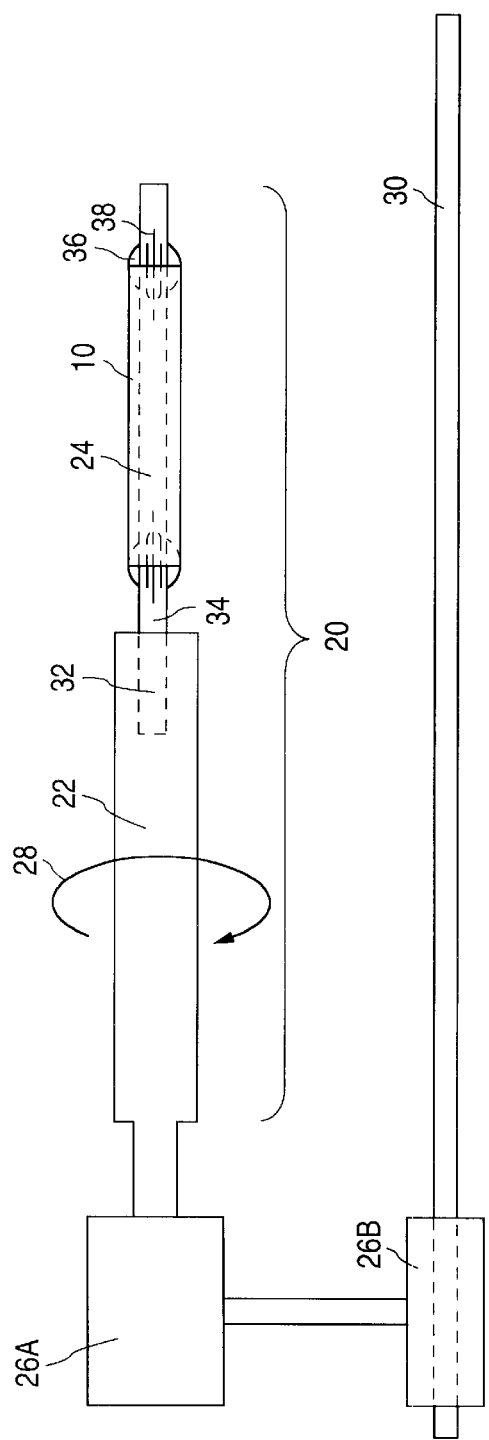
FIG. 2 illustrates a mounting assembly for supporting a stent.

Referring to FIG. 2, a mounting assembly 20 for supporting stent 10 is illustrated to include a support member 22 and a mandrel 24. Support member 22 can connect to a motor 26A so as to provide rotational motion about the longitudinal axis of stent 10, as depicted by arrow 28, during the coating process. Another motor 26B can also be provided for moving support member 22 in a linear direction, back and forth, along a rail 30. In accordance with one embodiment, mandrel 24 can be permanently affixed to support member 22. In accordance with another embodiment, support member 22 can include a bore 32 for receiving a first end 34 of mandrel 24. Bore 32 should be deep enough to allow mandrel 24 to securely mate with support member 22 so as to prevent movement of stent 10 on mounting assembly 20. First end 34 of mandrel 24 can be threaded so as to screw into bore 32 of support member 22.

As depicted in FIGS. 2 and 3, mounting assembly 20 supports stent 10 via protrusions or spines 36 disposed on mandrel 24, so as to provide a space between the outer surface of mandrel 24 and the inner surface of stent 10. Spines 36 are shown in greater detail in FIGS. 4A and 4B. Spines 36 can be made of any suitable material, and are typically made of the same material as mandrel 24. Examples of such suitable materials include stainless steel and polytetrafluoroethylene (e.g., TEFLON). While spines 36 are depicted herein as having a curved or semi-circular shape, spines 36 can be custom shaped to suit stents of various types. The shape of spines 36 can affect the retention of stent 10 on mandrel 24, the ease with which stent. 10 can be mounted and dismounted, and the degree of surface contact with stent 10. Sharp, pointed, and/or angular spines 36 can provide for a reduction in potential coating defects by providing a very small surface area at which stent 10 is in physical contact with spines 36. However, sharp, pointed, and/or angular spines 36 can snag struts 12, making mounting and dismounting of stent 10 more difficult. Spines 36 can be of any suitable size depending on the dimensions of the particular stent 10 to be supported. By way of example, to support stent 10 having a length of about 0.315 inches (about 8 mm) and an unexpanded internal diameter of about 0.035 inches (about 0.889 mm), which has been expanded to about 0.075 inches (about 1.905 mm) on mandrel 24 (having an outer diameter of 0.040 inches (about 1.016 mm)), spines 36 can have a width w from about 0.005 inches to about 0.007 inches (about 0.127 mm to about 0.178 mm) and a height h of about 0.017 inches (about 0.432 mm).

Mandrel 24 can have any suitable number of sets of spines 36. Each set of spines 36 can include any suitable number of individual spines 36. The particular number of sets, number of spines 36 within each set, arrangement of spines 36, distance between the sets, and distance between individual spines 36 in each set depend on the design of stent 10 to be supported. For example, if two sets of spines 36 are used to support stent 10 with a length of about 0.315 inches (about 8 mm), the distance between each set can be about 0.318 inches (about 8.1 mm).

Figure 5:
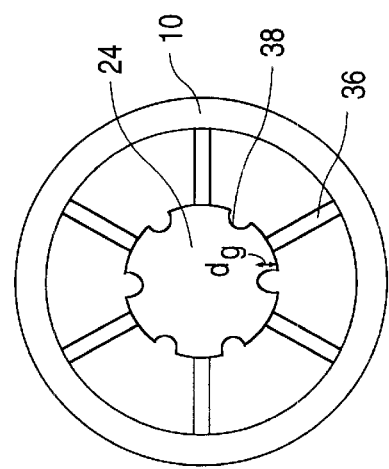
FIG. 5 is an end view of the spines-stent interface in FIG. 3.
Figure 1:
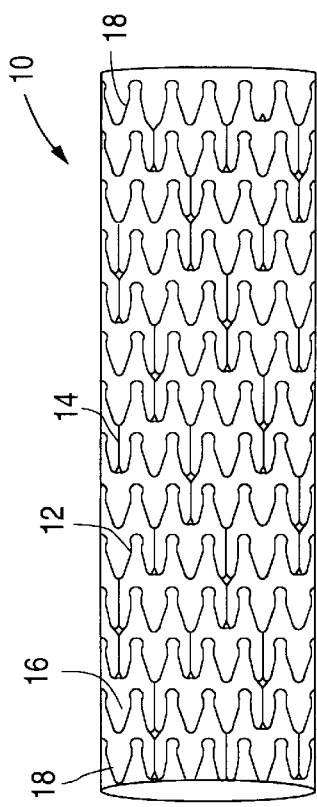
FIG. 1 illustrates a conventional stent.

In accordance with another embodiment, mounting assembly 10 can include grooves 38. Grooves 38 function to draw excess coating material away from stent 10 during the coating process, thereby further reducing the potential for pooling and other coating defects due to the excess coating material. Grooves 38 can be disposed between spines 36 and/or along the length of mandrel 24. Grooves 38 can be of any suitable length $l_g$ as shown in FIG. 4A, any suitable depth $d_g$ as shown in FIG. 5, and any suitable shape to facilitate receipt and containment of the excess coating material. By way of example, grooves 38 can have length $l_g$ from about 0.005 inches to about 1.5 inches (0.127 mm to about 38.1 mm) and depth $d_g$ from about 0.001 inches to about 0.002 inches (0.025 mm to about 0.051 mm).

Coating a Stent Using the Stent Mounting Assembly

The following method of application is being provided by way of illustration and is not intended to limit the embodiments of mounting assembly 20 of the present invention. By way of illustration, a spray apparatus, such as EFD 780S spray device with VALVEMATE 7040 control system (manufactured by EFD Inc., East Providence, R.I.), can be used to apply a composition to stent 10. EFD 780S spray device is an air-assisted external mixing atomizer. The composition is atomized into small droplets by air and uniformly applied to the stent surfaces. The atomization pressure can be maintained at a range of about 5 psi to about 20 psi. The droplet size depends on such factors as viscosity of the solution, surface tension of the solvent, and atomization pressure. Other types of spray applicators, including air-assisted internal mixing atomizers and ultrasonic applicators, can also be used for the application of the composition.

During the application of the composition, stent 10 supported by mounting assembly 20 can be rotated about the stent's central longitudinal axis. Rotation of stent 10 can be from about 1 rpm to about 300 rpm, more narrowly from about 50 rpm to about 150 rpm. By way of example, stent 10 can rotate at about 120 rpm. Stent 10 can also be moved in a linear direction along the same axis. Stent 10 can be moved at about 1 mm/second to about 12 mm/second, for example about 6 mm/second, or for a minimum of at least two passes (i.e., back and forth past the spray nozzle). The flow rate of the solution from the spray nozzle can be from about 0.01 mg/second to about 1.0 mg/second, more narrowly about 0.1 mg/second. Multiple repetitions for applying the composition can be performed, wherein each repetition can be, for example, about 1 second to about 10 seconds in duration. The amount of coating applied by each repetition can be about 0.1 micrograms/cm$^2$ (of stent surface) to about 10 micrograms/cm$^2$, for example less than about 2 micrograms/cm$^2$ per 5-second spray.

Each repetition can be followed by removal of a significant amount of the solvent(s). Depending on the volatility of the particular solvent employed, the solvent can evaporate essentially upon contact with stent 10. Alternatively, removal of the solvent can be induced by baking stent 10 in an oven at a mild temperature (e.g., 60° C.) for a suitable duration of time (e.g., 2–4 hours) or by the application of warm air. The application of warm air between each repetition prevents coating defects and minimizes interaction between the active agent and the solvent. The temperature of the warm air can be from about 30° C. to about 60° C., more narrowly from about 40° C. to about 50° C. The flow rate of the warm air can be from about 20 cubic feet/minute (CFM) (0.57 cubic meters/minute (CMM)) to about 80 CFM (2.27 CMM), more narrowly about 30 CFM (0.85 CMM) to about 40 CFM (1.13 CMM). The warm air can be applied for about 3 seconds to about 60 seconds, more narrowly for about 10 seconds to about 20 seconds. By way of example, warm air applications can be performed at a temperature of about 50° C., at a flow rate of about 40 CFM, and for about 10 seconds. Any suitable number of repetitions of applying the composition followed by removing the solvent(s) can be performed to form a coating of a desired thickness or weight. Excessive application of the polymer can, however, cause coating defects.

Operations such as wiping, centrifugation, or other web clearing acts can also be performed to achieve a more uniform coating. Briefly, wiping refers to the physical removal of excess coating from the surface of stent 10; and centrifugation refers to rapid rotation of stent 10 about an axis of rotation. The excess coating can also be vacuumed off of the surface of stent 10.

In accordance with one embodiment, stent 10 can be at least partially pre-expanded prior to the application of the composition. For example, stent 10 can be radially expanded about 20% to about 115%, for example about 112%—the measurement being taken from the stent's inner diameter at an expanded position as compared to the inner diameter at the unexpanded position. The expansion of stent 10, for increasing the interspace between stent struts 12 during the application of the composition, can further prevent "cob web" formation between the stent struts 12.

In accordance with one embodiment, the composition can include a solvent and a polymer dissolved in the solvent and optionally a wetting fluid. The composition can also include active agents, radiopaque elements, or radioactive isotopes. Representative examples of polymers that can be used to coat stent 10 include ethylene vinyl alcohol copolymer (commonly known by the generic name EVOH or by the trade name EVAL), poly(hydroxyvalerate); poly(L-lactic acid); polycaprolactone; poly(lactide-co-glycolide); poly (hydroxybutyrate); poly(hydroxybutyrate-co-valerate); polydioxanone; polyorthoester; polyanhydride; poly (glycolic acid); poly(D,L-lactic acid); poly(glycolic acid-co-trimethylene carbonate); polyphosphoester; polyphosphoester urethane; poly(amino acids); cyanoacrylates; poly (trimethylene carbonate); poly(iminocarbonate); copoly (ether-esters) (e.g. PEO/PLA); polyalkylene oxalates; polyphosphazenes; biomolecules, such as fibrin, fibrinogen, cellulose, starch, collagen and hyaluronic acid; polyurethanes; silicones; polyesters; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; rayon; rayon-triacetate; cellulose; cellulose acetate; cellulose butyrate; cellulose acetate butyrate; cellophane; cellulose nitrate; cellulose propionate; cellulose ethers; and carboxymethyl cellulose.

"Solvent" is defined as a liquid substance or composition that is compatible with the polymer and is capable of dissolving the polymer at the concentration desired in the composition. Examples of solvents include, but are not limited to, dimethylsulfoxide (DMSO), chloroform, acetone, water (buffered saline), xylene, methanol, ethanol, 1-propanol, tetrahydrofuran, 1-butanone, dimethylformamide, dimethylacetamide, cyclohexanone, ethyl acetate, methylethylketone, propylene glycol monomethylether, isopropanol, isopropanol admixed with water, N-methyl pyrrolidinone, toluene, and combinations thereof.

The active agent can be for inhibiting the activity of vascular smooth muscle cells. More specifically, the active agent can be aimed at inhibiting abnormal or inappropriate migration and/or proliferation of smooth muscle cells for the inhibition of restenosis. The active agent can also include any substance capable of exerting a therapeutic or prophylactic effect in the practice of the present invention. For example, the agent can be for enhancing wound healing in a vascular site or improving the structural and elastic properties of the vascular site. Examples of agents include antiproliferative substances such as actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin $I_1$, actinomycin $X_1$, and actinomycin $C_1$. The active agent can also fall under the genus of antineoplastic, antiinflammatory, antiplatelet, anticoagulant, antifibrin, antithrombin, antimitotic, antibiotic, antiallergic and antioxidant substances. Examples of such antineoplastics and/or antimitotics include paclitaxel (e.g. TAXOL® by Bristol-Myers Squibb Co., Stamford, Conn.), docetaxel (e.g. Taxotere®, from Aventis S.A., Frankfurt, Germany) methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.) Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax™ (Biogen, Inc., Cambridge, Mass.) Examples of such cytostatic or antiproliferative agents include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, genetically engineered epithelial cells, rapamycin and dexamethasone.

Examples of radiopaque elements include, but are not limited to, gold, tantalum, and platinum. An example of a radioactive isotope is $p^{32}$. Sufficient amounts of such substances may be dispersed in the composition such that the substances are not present in the composition as agglomerates or flocs.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A device for supporting a stent during the application of a coating material to the stent, comprising:

body configured to penetrate at least partially into the stent; and members protruding out from the body for preventing any contact between an inner surface of the stent and an outer surface of the body.

2. The device of claim 1, additionally including slots in the outer surface of the body for receiving some of the coating material that comes into contact with the body.

3. The device of claim 1, wherein the members are arranged about a circumference of the body.

4. The device of claim 1, wherein the members are circular in shape.

5. A mandrel for supporting a stent, comprising:
a body for being at least partially inserted in a hollow body of a stent;
at least two members projecting out of the body and capable of being in contact with an inner surface of the stent.

6. The mandrel of claim 5, wherein the at least two members are circular in shape.

7. The mandrel of claim 5, wherein a surface of the body does not contact the inner surface of the stent.

8. The mandrel of claim 5, additionally including grooves positioned in the body for receiving and containing excess coating substance applied to the stent.

9. A method of coating a stent, comprising:
positioning a stent over a mandrel having members projecting out of the mandrel, wherein at least one of the members is in contact with an inner surface of the stent; and
applying a coating material to the stent.

10. The method of claim 9, additionally including rotating the stent about a longitudinal axis of the stent.

11. The method of claim 9, wherein the act of applying comprises spraying a polymer added to a fluid, and optionally including an active agent, onto the stent.

12. The method of claim 11, wherein the active agent is for the management of restenosis.

13. The device of claim 1, wherein the members protruding out from the body are curved in shape.

14. The device of claim 1, wherein the members protruding out from the body comprise individual protruding members.

15. The device of claim 1, wherein the body and the members protruding out from the body are fabricated from stainless steel.

16. The device of claim 1, wherein the body and the members protruding out from the body are fabricated from polytetrafluoroethylene.

17. The device of claim 2, wherein the slots are disposed between the members protruding out from the body.

18. The device of claim 17, wherein the slots extend along the length of the body.

19. The device of claim 1, wherein the body comprises a threaded first end.

20. The device of claim 19, wherein the threaded first end of the body screws into a bore in a support member.

21. A method of coating a stent, the method comprising the steps of:
inserting a body at least partially into a stent, wherein the body includes members protruding therefrom for preventing any contact between an inner surface of the stent and an outer surface of the body; and
applying a coating material to the stent.

22. The method of claim 21, wherein the step of inserting the body comprises inserting a mandrel at least partially into the stent.

23. The method of claim 21, wherein the step of applying a coating material comprises spraying a polymer, added to a fluid, and optionally including an active agent, onto the stent.

24. The method of claim 21, further comprising rotating the stent about the longitudinal axis of the stent.

* * * * *